United States Patent [19]
Heywang-Koebrunner et al.

[11] Patent Number: 5,678,549
[45] Date of Patent: Oct. 21, 1997

[54] STEREOTACTIC AUXILIARY ATTACHMENT FOR A NUCLEAR MAGNETIC RESONANCE TOMOGRAPHY APPARATUS

[75] Inventors: Sylvia Heywang-Koebrunner, Leipzig; Wilhelm Hanke, Rueckersdorf, both of Germany

[73] Assignee: Siemens Aktiengesellschaft, Munich, Germany

[21] Appl. No.: 98,828

[22] Filed: Jul. 29, 1993

[30] Foreign Application Priority Data

Jul. 29, 1992 [DE] Germany ............... 42 25 001.3

[51] Int. Cl.$^6$ .................................................. A61B 5/055
[52] U.S. Cl. ............................... 128/653.5; 606/130
[58] Field of Search ...................... 128/653.2, 653.5, 128/662.05, 653.4; 324/309, 318, 322; 606/130

[56] References Cited

U.S. PATENT DOCUMENTS 4,608,991  9/1986  Rollwitz .
4,981,142  1/1991  Dachman ................... 128/749

FOREIGN PATENT DOCUMENTS 3140225  4/1983  Germany ............... 128/653.2

OTHER PUBLICATIONS

"Preoperative Needle–Marking of Nonpalpable Breast Lesions," Olesen et al., Fortschr. Röntgenstr. 131.3 (1979), pp. 331–332.

"Möglichkeiten der Magnetresonanztomographie in der Diagnostik nicht pappabler Mammatumoren," Zapf et al., Fortschr. Röntgenstr. 154.1 (1991) pp. 106–110.

*Primary Examiner*—Ruth S. Smith
*Attorney, Agent, or Firm*—Hill, Steadman & Simpson

[57] ABSTRACT

A stereotactic auxiliary attachment for a nuclear magnetic resonance tomography apparatus for use in conducting mammographic examinations wherein a needle localization of a breast mass or needle marking of a breast mass are implemented with high precisions includes two parallel compressions plates mounted so as to be displaceable relative to one each other, and between which an examination subject such as breast, can be compressed. At least one of the plates has a reception coil of the magnetic resonance tomography apparatus allocated thereto, and at least one of the plates has holes therein for the introduction of a biopsy or marking needle. One of both of the plates can be provided with markings which are identifiable in the magnetic resonance image (tomogram).

33 Claims, 5 Drawing Sheets

STEREOTACTIC AUXILIARY ATTACHMENT FOR A NUCLEAR MAGNETIC RESONANCE TOMOGRAPHY APPARATUS

BACKGROUND OF THE INVENTION

1. Field of the Invention

The present invention is directed to a stereotactic auxiliary unit for attachment to a nuclear magnetic resonance tomography apparatus, and particularly to such unit for stereotactic localization of masses, lesions, or other items of interest contained in a magnetic resonance tomographic image of a patient.

2. Description of the Prior Art

Contrast agent nuclear magnetic resonance tomography has increasingly proven to be a valuable, new supplementary method for mammographic diagnostics, as described in the article "Magnetic Resonance Tomography Magnetresonanztomographie in der Diagnostik nicht palpabler Mammatumoren," Zapf et al., Fortsch. Rontgenstr. 154.1 (1991), pages 106–110. In comparison to established methods, such as x-ray mammography, sonography and clinical examinations, contrast agent nuclear magnetic resonance tomography is significantly more sensitive, particularly for identifying masses in dense tissue which is difficult to evaluate.

Without contrast enhancement, contrast nuclear magnetic resonance tomography is highly specific for malignant tumor exclusion. With focal contrast enhancement the specificity of contrast agent nuclear magnetic resonance tomography is not as good for further differentiation between benign and malignant masses. Focal contrast enhancement can identify a carcinoma which, to the extent it is visible only in an NMR tomogram, can be found earlier using contrast agent nuclear magnetic resonance tomography than with other methods. Focal contrast enhancement, however, may also be caused by benign tumors or proliferative mastopathies. The proportion of carcinoma discovered using data produced NMR-tomographically is comparable to the proportion of carcinoma in data obtained by other mammographic examination techniques, which are also usually unspecific.

In order to obtain the diagnostic advantage of the significantly greater sensitivity of contrast agent nuclear magnetic resonance tomography, however, a precise localization of an item of interest in the examination subject itself is particularly important, for several reasons.

First, items found only NMR-tomographically are non-palpable, and are generally extremely small. These items do not contain any microcalcifications, which would be detectable by specimen radiography. Therefore, such items are very difficult for surgeons and pathologists to find within the examination subject itself, without further auxiliary means.

Secondly, it would be helpful to be able to undertake a clarification or confirmation of the status (benign or malignant) of the identified item by punction cytology or puncture histology, in order to avoid unnecessary surgical excision of a biopsy sample of a benign item, which was discovered only NMR-tomographically. Surgical excision biopsy could then be reserved for truly suspicious items which are discovered NMR-tomographically.

It is therefore desirable in the conduct of breast examinations by NMR tomographic means to be able to provide a precise stereotactic localization of findings within a breast.

As is known, due to its compressibility, the breast must be fixed with a slight compression in order to undertake a stereotactic localization. The article "Preoperative Needle-marking of Non-palpable Breast Lesions," Oleson et al., Fortschr. Roentgenstr. 131.3 (1979), pages 331–332, describes a stereotactic means utilized in conjunction with mammography x-ray. This stereotactic means includes compression plates, one of which has a checkerboard arrangement of holes therein for needle marking. This apparatus is applied with the patient standing upright. The fashioning and arrangement of the plates are matched to the specific requirements of an x-ray apparatus.

For conducting an NMR-tomographic examination of the breast, it is currently preferred that the patient be in a prone position, as described in the earlier-cited Zapf et al. article. A nuclear magnetic resonance tomography apparatus which is specifically suited for mammographic examinations is disclosed in U.S. Pat. No. 4,608,991, wherein the patient is arranged in a prone position. For conducting the examination, the breast is received in a depression in the patients support, so that a relatively good positional fixing of the breast is achieved. The depression, however, is not itself accessible due to the overall arrangement of the magnetic resonance apparatus, and moreover the breast is not accessible due to the reception coils surrounding the depression.

SUMMARY OF THE INVENTION

It is an object of the present invention to provide an auxiliary attachment for a nuclear magnetic resonance tomography apparatus for conducting an mammographic examination, by means of which the examination subject can be fixed in position, while still permitting the examination subject to be accessible and permitting a precise, stereotactic localization of NMR-tomographic findings.

The above object is achieved in accordance with the principles of the present invention in a stereotactic auxiliary attachment for a nuclear magnetic resonance tomography apparatus having two parallel compression plates mounted so as to be displaceable relative to each other, and between which a breast can be fixed and compressed. At least one of the compression plates has a reception coil for the nuclear magnetic resonance apparatus allocated thereto in a spatially defined manner, and at least one of the compression plates has a plurality of holes therein for the introduction of a needle. The auxiliary attachment of the invention must fulfill a plurality of functions. The examination subject must be capable of being fixed between the compression plates, and a reception coil of the nuclear magnetic resonance tomography apparatus must be allocated in a spatially known manner to at least one of the compression plates, otherwise an adequate image quality for the presentation of the NMR findings which are to be localized is not possible. In order to implement needle punctures for pre-operative markings or for cytological or histological examination of lesions discovered by means of the NMR tomogram, it must be assured that the lesion (mass) is both accessible and able to be reproducibly located, given a breast which is fixed in position.

The parallel arrangement and the displaceability of the compression plates in the attachment of the invention permit the examination subject to be individually compressed until an adequate positional fixing is achieved.

Moreover, in order to permit medial findings to be medially marked while also permitting lateral findings to be laterally marked in a pre-operative marking procedure corresponding to the route of surgical access, the auxiliary attachment of the invention is structured in a first embodiment so that it can be employed mirror-inverted, with the patient lying on her left or right side.

The localization of the finding in the NMR image is enabled by the knowledge of the position of the sectional plane of the tomogram, and on the basis of orientation means which are usually present in nuclear magnetic resonance tomography systems. Such orientation means can, for example, be a light-beam localizer or can be a marker consisting of material which is visible in the NMR tomogram and which is located in the detection region of the coil, which serves as a fixed reference for making spatial measurements. If such an orientation means is not present in an existing NMR apparatus with which the auxiliary attachment of the invention is to be used, or if the precision of the existing orientation means is not adequate, a further embodiment of the invention provides a marking element which is visible in the tomography image and which is disposed in the detection region of the reception coil. The spatial coordinates of the NMR finding can be unambiguously defined on the basis of such a marking means or spacing measurement relative to other points of reference in the nuclear magnetic resonance tomography apparatus.

The marking means may be separate from the compression plate of the invention, or may be arranged attached to or in one or both of the compression plates. Preferably, the marking means is in the form of a chamber filled with an NMR-tomographically detectable substance such as, for example, gadolinium-DTPA or copper sulfate. The chamber having the NMR-tomographically detectable substance therein can be fashioned as a cavity in one of the compression plates. It is also possible to fashion the chamber as a small tube or capsule arranged on one of the compression plates. The small tube or capsule can be attached to that side of the a compression plate facing toward the examination subject, or to a side of a compression plate facing away from the examination subject.

Preferably, however, the chamber has a configuration which limits the examination region of the reception coil, and forms a substantially closed frame or loop, preferably a rectangular frame or loop. In this embodiment, the chamber is preferably disposed in the plane of one of the compression plates. If one or both of the compression plates are equipped with such a frame, and if the tomogram is taken in a section plane disposed perpendicularly relative to the plates, the marking frame will thus also be perpendicularly cut, and will be visible on a monitor, or in whatever form the tomogram is displayed or registered.

Alternatively, the chamber containing the NMR-tomographically detectable substance can be shaped as a cruciform chamber, which proceeds through the center of the region of the compression plate which is limited by the reception coil.

Since a plurality of holes for introducing a needle are provided in at least one compression plate, an exact needle introduction into the examination subject, matched to the tomographic image is made possible. The holes can be distributed over the entire compression plate, or can be provided within the plate region limited by the reception coil.

The holes are preferably arranged in the compression plates in rows having a defined spacing. The hole pattern may have a closer arrangement of holes in specific regions, so that different hole patterns can be selected for the most advantageous use with a particular examination subject.

The compression plates are preferably secured to a common holder, which may be in the form of a rod perpendicularly secured to the patient support, and along which the plates are adjustable in a vertical direction so as to be adaptable to the position of the examination subject. The holder can be attached either to the left or right side of the patient support, so that an examination is possible with the patient lying on her right or on her left side. The rod can be fashioned as a rail, which interacts with corresponding fastening devices attached to each compression plate, for fixing the plates to the holder. The holder can also include the electrical leads for the reception coil, so that no separate table leads to the compression plate or plates are required, which could possibly restrict the mobility of the compression plates. Moreover, the holder can be provided with a measuring scale in order to be able to read the position of the compression plates.

Helmholtz-like or other suitable surface coils can be utilized as the reception coils, having one or more turns, with the turns having a relatively large diameter. Helmholtz coil arrangements can be simultaneously utilized as the transmission coil, because of their relatively uniform characteristic. In a preferred embodiment, the turn or turns of the coil arrangement is/are disposed on the exterior of the compression plate, and are secured at that location. The coil arrangement may, however, alternatively be integrated within the compression plate. It is also possible to secure the reception coil to a separate holder, or to attach it to the compression plate in a hinged fashion, so that the coil can be pivoted to standby position after the image has been obtained.

In order to avoid the compression plates influencing or disturbing the generation of the NMR-tomographic image, the plates consist of materials such as, for example, plastic which does not disturb the imaging.

DESCRIPTION OF THE PREFERRED EMBODIMENTS

Figure 1:
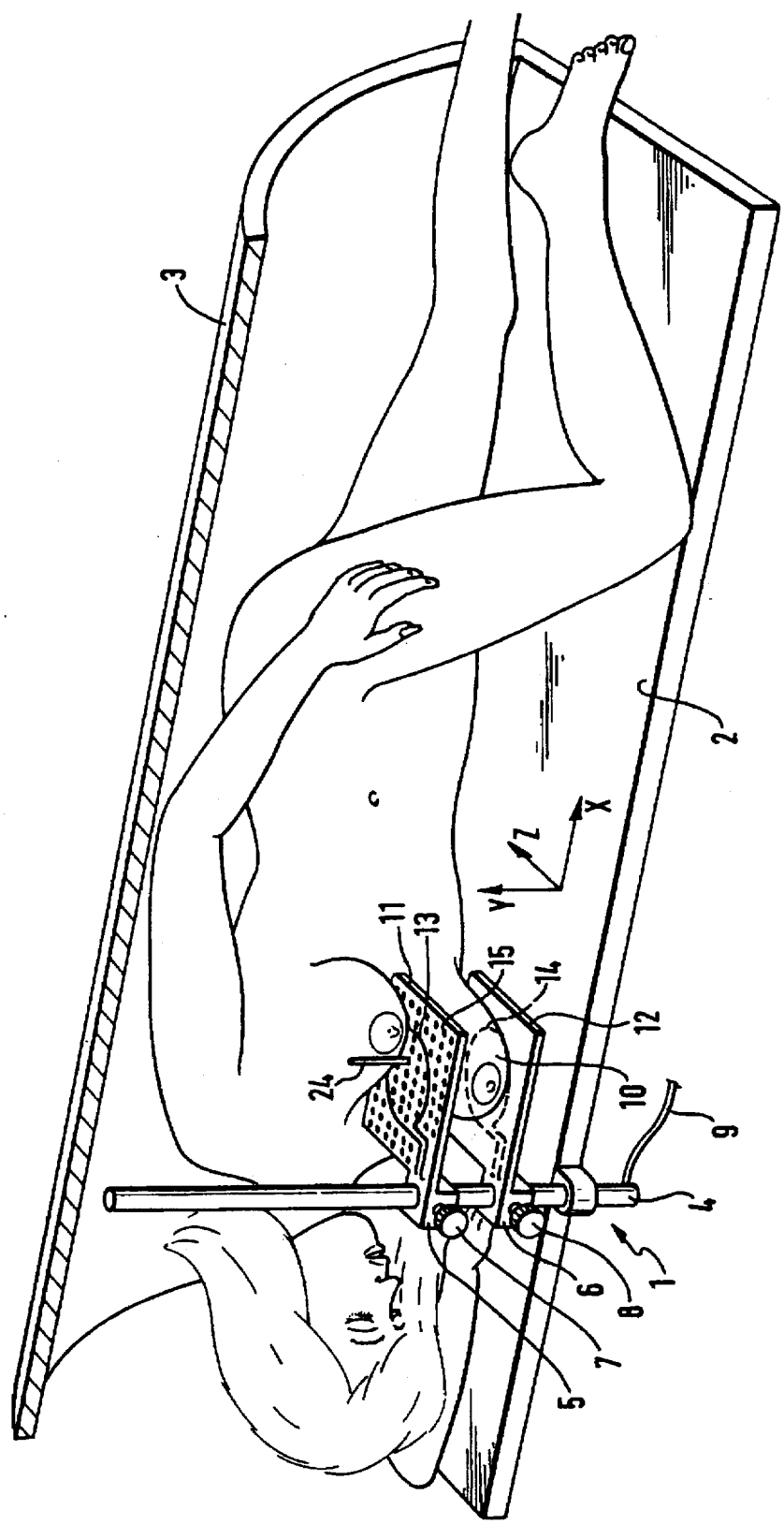
FIG. 1 is a perspective view of an auxiliary attachment for a nuclear magnetic resonance tomography apparatus constructed in accordance with the principles of the present invention, in use for conducting a mammographic examination.

The examination volume (tunnel) 3 surrounding a patient support 2 in a nuclear magnetic resonance tomography apparatus (not otherwise shown) is schematically shown in FIG. 1. A patient lying on her side is located on the patient support 2 for conducting an NMR-tomographic examination of the right breast, the right breast constituting the examination subject 10. An auxiliary attachment 1, which includes a holder in the form of at least one rod as well as two compression plates 11 and 12 is attached to the patient support 2. The lower end of the rod 4 is secured to the patient support 2. The compression plates 11 and 12, which are horizontally oriented in the embodiment of FIG. 1, are equipped with fastening devices 5 and 6 having respective knobs 7 and 8, which can be turned to loosen and tighten the fastening devices 5 and 6, relative to the rod 4, thereby permitting the compression plates 11 and 12 to be both displaceable in the vertical direction, and to be fixed at selected locations along the rod 4. An electrical lead 9 for supplying power to reception coils 13 and 14, respectively arranged on the compression plates 11 and 12, is disposed at the lower end of the rod 4. The two coils 13 and 14 disposed opposite one other form a Helmholz arrangement. The upper compression plate 11 has a plurality of holes 15, through which a needle 24, such as a biopsy needle, can be introduced into the examination subject 10.

Figure 2:
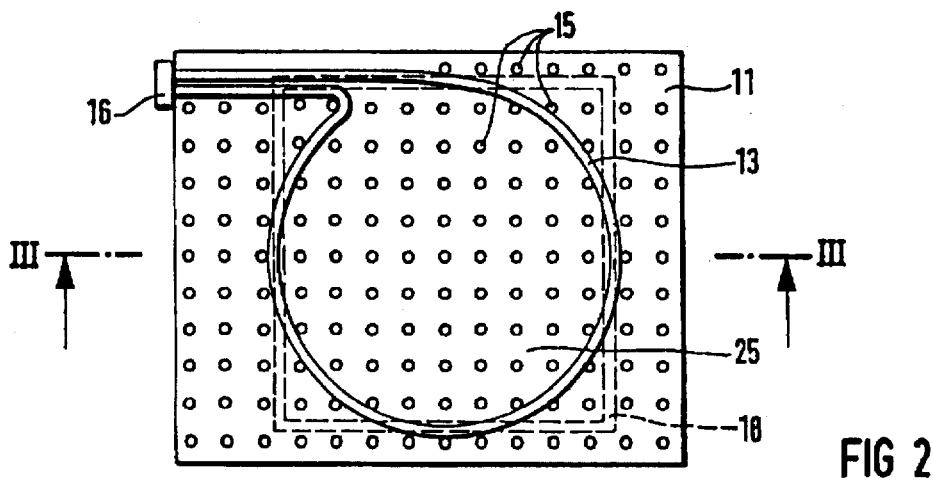
FIG. 2 is a plan view of the upper plate of the auxiliary attachment shown in FIG. 1.

A plan view of the compression plate 11 is shown in FIG. 2. The coil 13, which is composed of only one turn in this embodiment, is secured on the surface of the compression plate 11. The coil 13 is conducted substantially to the edge of the compression plate 11, at which location an electrical terminal 16 is attached which interacts with a corresponding device at the rod for producing an electrical contact. The entire compression plate 11 is provided with a hole pattern, with the holes 15 being arranged in rows and columns at constant spacings.

Figure 3:
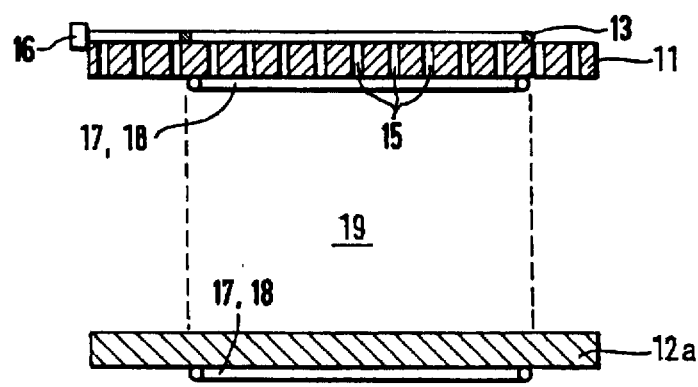
FIG. 3 is a sectional view taken through the upper plate of the apparatus along III—III of FIG. 2, together with a sectional view of a further embodiment of a lower plate.

A section along the line III—III of the compression plate 11 is shown in FIG. 3, which also shows a further embodiment of a lower compression plate 12a disposed below the compression plate 11. The examination region of the reception coil 13 is identified approximately by the dashed-line region 19. Marking means in the form of a chamber 17 filled with an NMR-topographically detectable substance are provided in the form of a tube 18 located at the underside of the compression pate 11, within the examination region 19. The marking tube 18 is closed, and limits the examination region 19 of the reception coil 13 in the horizontal direction.

The lower compression plate 12a shown in FIG. 3 has no holes, and carries no reception coil. A second marking means 17, also formed by a tube 18, is disposed on the underside of the plate 12a in registry with the tube 18 on the plate 11. The tube 18 on the compression plate 12a is not located in the examination region 19, but is still within the detection region of the reception coil 13.

Figure 4:
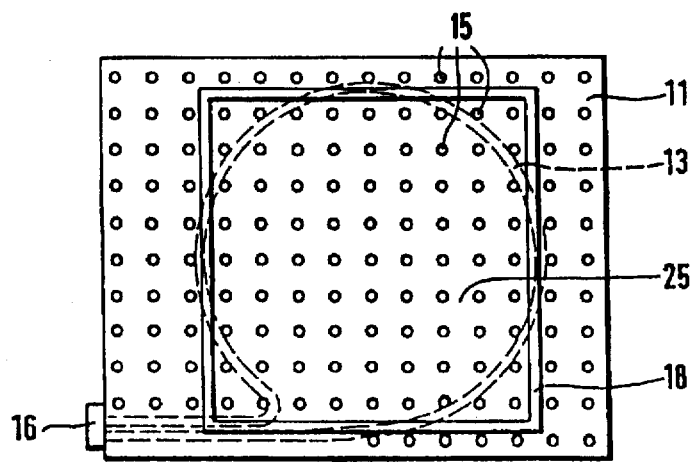
FIG. 4 is a bottom view of the upper plate shown in FIG. 2.

A bottom view of the compression plate 11 is shown in FIG. 4, wherein the closed, rectangular loop or frame of the tube 18 can be clearly seen. The holes 15 are arranged in a region 25 within the frame 18.

Figure 6:
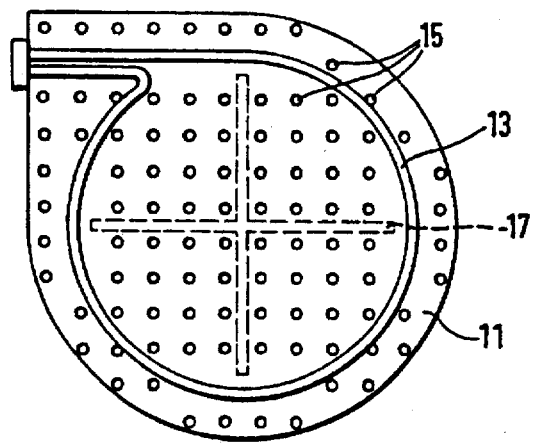
FIG. 6 is a plan view of a compression plate for use in a further embodiment of the invention.
Figure 5:
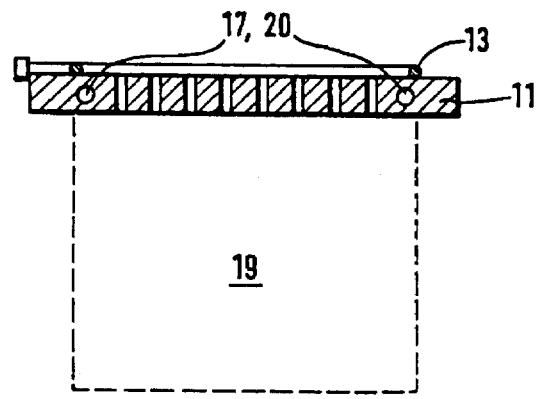
FIG. 5 is a section taken through a compression plate in a further embodiment of the invention.

Another embodiment of the compression plate 11 is shown in FIG. 6. In this embodiment, the plate is round, and the marking means 17 has a cruciform shape.

Figure 7:
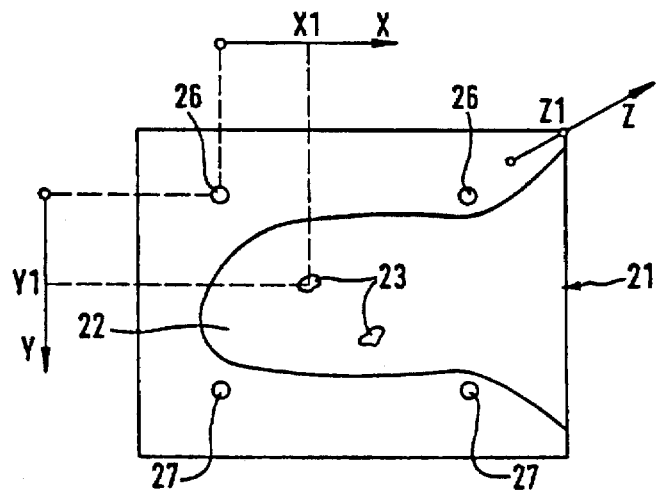
FIG. 7 is a schematic illustration of a tomography image obtained using the auxiliary attachment of the invention.

A tomographic image obtained in accordance with the principles of the present invention is shown in FIG. 7. The three spatial directions, x, y and z are also shown in FIG. 1, so that it is clear that the image 21 shown in FIG. 7 represents a tomogram of the examination subject 10 disposed perpendicularly relative to the compression plates 11 and 12. The examination subject 10 is shown in the image 21 as a tomogram 22, and the marking chambers of the plates 11 and 12 (or 12a) are in the form of round images 26 and 27 at the corners of the examination region 19. The examination subject 10, shown as the tomogram 22 within the examination region, is thereby marked. Because the position of the tomographic image 21 is defined by the slice position, the z-coordinate Z1 is fixed. The two other coordinates X1 and Y1 of a lesion or mass 23 can be identified on the basis of the tomographic image 21 with reference to the corner points 26 and 27, so that both a corresponding hole 15 in the upper compression plate 11 and the penetration depth of a needle 24 (shown in FIG. 1) can be identified on the basis of the spatial coordinates calculated in this manner. Because the examination subject is non-displaceably fixed between the compression plates 11 and 12 (or 12a) a needle puncture can thus be subsequently implemented with high precision.

Figure 8:
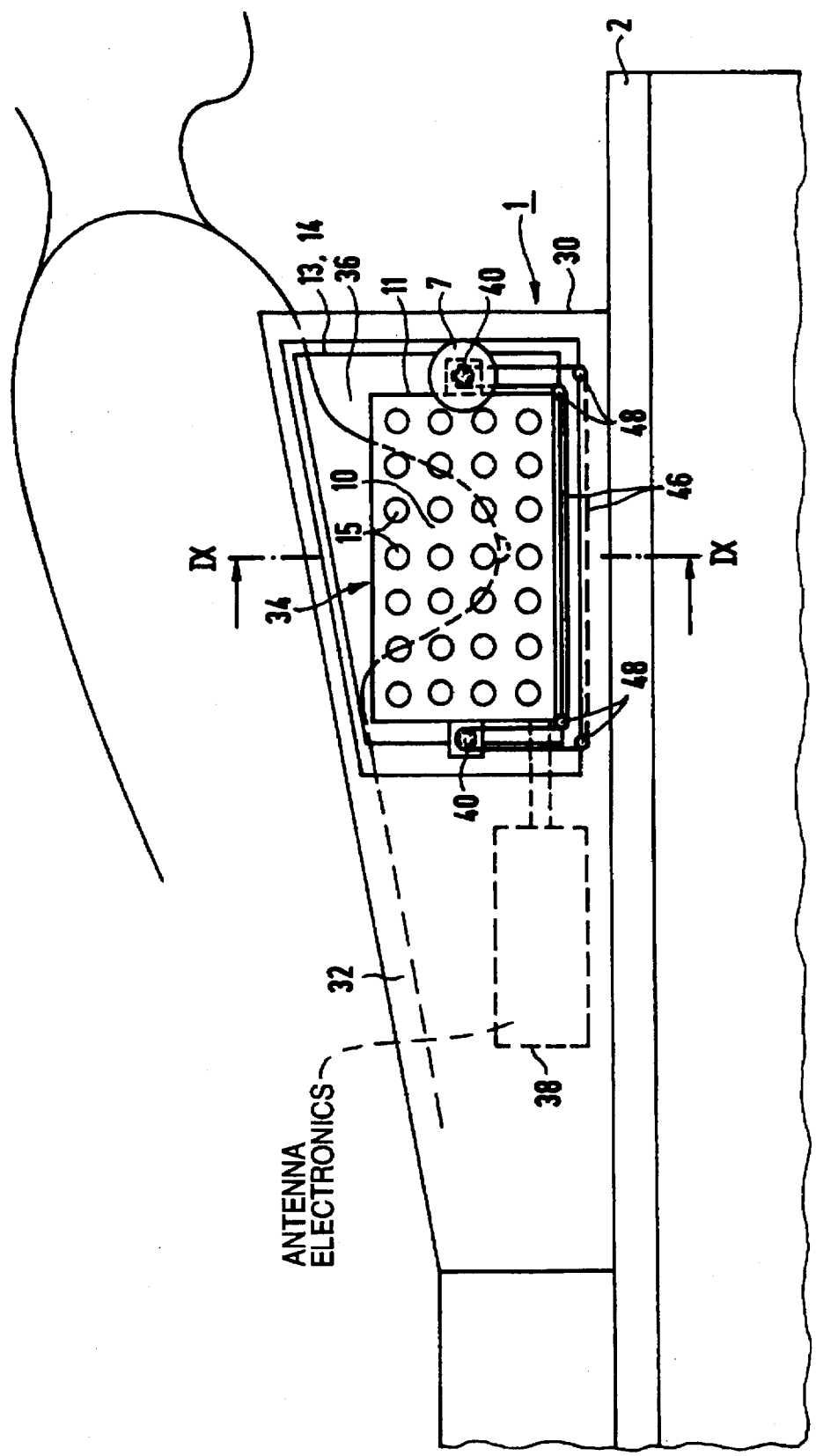
FIG. 8 is a side elevational view of a further embodiment of an auxiliary attachment constructed in accordance with the principles of the present invention.
Figure 9:
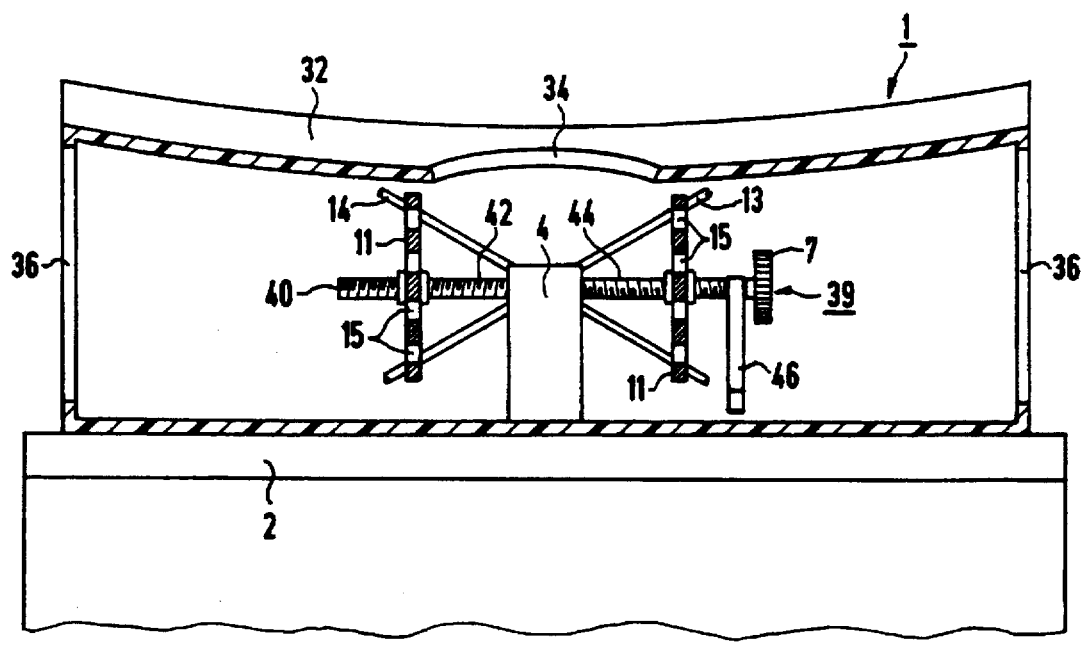
FIG. 9 is a sectional view of the embodiment of FIG. 8, taken along line IV—IV.

A further embodiment of the auxiliary attachment of the invention is shown in FIGS. 8 and 9, for examining a patient in the prone position. The two compression plates 11 are vertically arranged in this embodiment, and are provided with holes 15. The accessibility to the perforated compression plates 11 in this examination position is achieved by fashioning the auxiliary attachment 1 in the form of a crown or projection on the top of the patient support 2. To that end, the auxiliary attachment 1 includes a housing 30, having an upper side forming a bed surface 32 for the patient. The bed surface 32 has a recess 34 provided for the acceptance of the breasts, as the examination subject 10. The perforated compression plates 11 are disposed within the housing at the sides of the recess 34, and are accessible through two openings 36 in the lateral sides of the housing 30. A hand wheel 7 is provided as a manual drive for simultaneous adjustment of the two compression plates 11 in opposite directions, which can be operated through one of the openings 36.

The examination subject 10, including the compression plates 11, is surrounded by an antenna arrangement. A circularly polarizing antenna arrangement is used in this embodiment, in the form of two crossed coils 13 and 14. Each of the coils 13 and 14 is composed of a quadrilateral turn. As warranted, the turns can alternatively be circular or elliptical, for adaptation to the anatomy of the examination subject 10. The two coils 13 and 14 are connected to antenna electronics 38 contained within the housing 30. The antenna electronics 38 combines the reception signals from the coils 13 and 14 after phase-shifting the signals from one of the coils by 90° phase shift relative to the signals from the other coil, and then pre-amplifies the combined signals. The combined, phase-shifted combined and pre-amplified signals are supplied as an output of the antenna electronics 38.

The coils 13 and 14 and the compression plates 11 are mounted independently of each other, so that the reception properties of the two crossed coils 13 and 14, forming the circularly polarizing antenna arrangement are not modified in the event of adjustment of the compression plates 11.

An actuation unit 39 for adjusting the two compression plates 11 in opposite directions is arranged at the mount 4, this actuation unit 39 being formed by two threaded rods 40. The threaded rods 40 are provided with opposed threads 42 and 44, which engage corresponding cooperating, laterally arranged threads in the compression plates 11.

For simultaneous and opposed adjustment of the two compression plates 11, the threaded rods 40 are connected to each other by means of a toothed belt 46. The rotary knob 7 for the actuation unit 39 is directly secured to an extension of one of the threaded rod 40, with the other threaded rod 40 being actuated by the toothed belt 46. The toothed belt 46 is conducted around deflection rollers 48, so that it does not impede accessibility to the compression plates 11.

The sectional view of the auxiliary attachment of FIG. 8 along line IX—IX, shown in FIG. 9 shows that the recess 34 is disposed symmetrically relative to the openings 36. Access to the examination subject 10 can thus proceed equally well from both sides via the holes 15 in the compression plates 11.

The above-described marking means are not separately shown in FIGS. 8 and 9, but will be understood to be arranged in the embodiment of FIGS. 8 and 9 within the detection region of the coils 13 in the manner described above. The marking means enable an exact localization in all three coordinate directions within the examination subject 10 in the nuclear magnetic resonance tomography image.

Although modifications and changes may be suggested by those skilled in the art, it is the intention of the inventors to embody within the patent warranted hereon all changes and modifications as reasonably and properly come within the scope of their contribution to the art.

We claim as our invention:

1. A stereotactic auxiliary attachment for a nuclear magnetic resonance tomography apparatus comprising:
   first and second compression plates;
   means for mounting said compression plates parallel to each other and for displacement relative to each other for permitting an examination subject to be disposed and compressed in a volume between said compression plates;
   at least one of said compression plates having a plurality of holes therein for permitting introduction of a needle into said examination subject; and
   a nuclear magnetic resonance tomography reception coil having a detection region;
   means for mounting said reception coil relative to said compression plates in a spatially defined manner with said detection region substantially containing said volume.

2. An auxiliary attachment as claimed in claim 1 wherein one of said compression plates comprises said means for mounting said reception coil by forming a carrier for said reception coil.

3. An auxiliary attachment as claimed in claim 1 wherein said means for mounting said reception coil in said spatially defined manner relative to said compression plates comprises means for mounting said reception coil independently of said compression plates.

4. An auxiliary attachment as claimed in claim 1 wherein said plurality of holes are arranged in said one of said compression plates in a regular pattern.

5. An auxiliary attachment as claimed in claim 1 wherein said compression plates consist of material which does not disturb the generation of a nuclear magnetic resonance tomographic image.

6. An auxiliary attachment as claimed in claim 1 wherein said compression plates consist of plastic.

7. An auxiliary attachment as claimed in claim 1 further comprising marking means for generating an element which is detectable in a nuclear magnetic resonance tomogram disposed in a detection region of said reception coil.

8. An auxiliary attachment as claimed in claim 7 wherein said marking means is disposed so as to extend through a plane oriented perpendicular relative to said compression plates.

9. An auxiliary attachment as claimed in claim 7 wherein said marking means is carried by at least one of said compression plates.

10. An auxiliary attachment as claimed in claim 9 wherein said marking means comprises a chamber filled with an NMR tomographically detectable substance.

11. An auxiliary attachment as claimed in claim 10 wherein said chamber is formed by a cavity in said one of said compression plates.

12. An auxiliary attachment as claimed in claim 10 wherein said chamber is formed by a tube disposed on said one of said compression plates.

13. An auxiliary attachment as claimed in claim 12 wherein said tube forms a closed frame surrounding an examination region of said reception coil.

14. An auxiliary attachment as claimed in claim 12 wherein said tube has a cruciform shape.

15. An auxiliary attachment as claimed in claim 10 wherein said NMR-tomographically detectable substance comprises gadolinium-DTPA.

16. An auxiliary attachment as claimed in claim 10 wherein said NMR-tomographically detectable substance comprises copper sulfate.

17. An auxiliary attachment as claimed in claim 10 wherein said chamber is formed by a capsule disposed on said one of said compression plates.

18. An auxiliary attachment as claimed in claim 1 wherein said means for mounting said compression plates include means for orienting said compression plates for fixing and compressing a breast of an examination subject disposed on her side.

19. An auxiliary attachment as claimed in claim 1 wherein said means for mounting said compression plates comprises means for mounting said compression plates horizontally oriented.

20. An auxiliary attachment as claimed in claim 1 wherein said means for mounting said compression plates comprises means for mounting said compression plates vertically oriented.

21. An auxiliary attachment as claimed in claim 1 wherein said means for mounting said compression plates comprises a common holder to which both compression plates are attached.

22. An auxiliary attachment as claimed in claim 21 wherein said reception coil has an electrical lead, and wherein said electrical lead is secured to said holder.

23. An auxiliary attachment as claimed in claim 1 wherein both of said compression plates have a plurality of holes therein.

24. An auxiliary attachment as claimed in claim 21 wherein said means for mounting includes means for displacing said compression plates in opposite directions relative to each other.

25. An auxiliary attachment as claimed in claim 24 wherein said means for displacing said compression plates comprises a manually operated drive for simultaneously displacing said compression plates in said opposite directions.

26. An auxiliary attachment as claimed in claim 25 wherein said means for displacing comprises two threaded rods having oppositely directed threads, respectively extending through threaded bores in said compression plates.

27. An auxiliary attachment as claimed in claim 1 comprising a further reception coil, and wherein said means for mounting said reception coil comprise mean for mounting said reception coil and said further reception coil in a combination forming a circularly polarizing coil arrangement.

28. An auxiliary attachment as claimed in claim 27 wherein means for mounting said reception coil comprise means for orienting said combination independently of said compression plates.

29. An auxiliary attachment as claimed in claim 27 wherein said coil arrangement has an interior volume, and wherein said compression plates are disposed in said interior volume.

30. An auxiliary attachment as claimed in claim 1 for use in a magnetic resonance imaging apparatus having a patient support, and further comprising a housing for said compression plates and means for attaching said housing on said support for accommodating a patient lying face-down, said housing having a recess for accepting the breasts of said patient, and said housing having lateral openings therein disposed for providing access to said compression plates in said housing.

31. An auxiliary attachment as claimed in claim 30 wherein said recess is disposed symmetrically relative to said lateral openings.

32. An auxiliary attachment as claimed in claim 1 wherein said means for mounting said reception coil comprise one of said compression plates, forming a carrier for said reception coil, and said auxiliary attachment further comprising a further reception coil carried by the other of said compression plates, and wherein said means for mounting said first and second compression plates comprise means for orienting said first and second compression plates with said reception coil and said further reception coil respectively carried thereby in an orientation forming a circularly polarizing coil arrangement.

33. A breast coil arrangement for use in obtaining a magnetic resonance image of a breast, comprising:
  means for compressing a breast to be imaged including first and second substantially planar MRI coils for placement on either side of said breast and
  first and second nonconductive coil supporting plates supporting said first and second coils; respectively, at least one of said plates including means for guiding placement of localizing needles into said breast.

* * * * *